United States Patent
Krebs et al.

(10) Patent No.: US 7,945,301 B2
(45) Date of Patent: *May 17, 2011

(54) METHODS AND APPARATUS FOR THE ADMINISTRATION OF CO

(75) Inventors: Christian Krebs, Vösendorf (AT); Rainer Müllner, Wr. Neudorf (AT)

(73) Assignee: Ikaria, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/502,991

(22) Filed: Jul. 14, 2009

(65) Prior Publication Data

US 2010/0012117 A1  Jan. 21, 2010

Related U.S. Application Data

(63) Continuation of application No. 10/520,270, filed as application No. PCT/EP03/06856 on Jun. 27, 2003, now Pat. No. 7,574,246.

(30) Foreign Application Priority Data

Jul. 4, 2002  (DE) .................................. 102 30 165

(51) Int. Cl.
*A61B 5/05*  (2006.01)
*A61M 31/00* (2006.01)
*F16K 31/02* (2006.01)
(52) U.S. Cl. ...................... 600/345; 604/66; 128/204.23
(58) Field of Classification Search .......................... None
See application file for complete search history.

(56) References Cited

U.S. PATENT DOCUMENTS

| 5,293,875 A | 3/1994 | Stone |
| 5,320,093 A | 6/1994 | Raemer |
| 5,429,123 A | 7/1995 | Shaffer |
| 5,810,723 A | 9/1998 | Aldrich |
| 5,979,443 A | 11/1999 | Dingley |

(Continued)

FOREIGN PATENT DOCUMENTS

| EP | 0524083 | 7/1992 |
| GB | 1581482 | 12/1980 |
| JP | 9108352 A | 4/1997 |
| RU | 2173082 CI | 9/2001 |
| RU | 2197281 C2 | 1/2003 |
| WO | WO 98/13058 A1 | 4/1998 |
| WO | WO 01/15762 A1 | 3/2001 |
| WO | WO 01/41856 | 6/2001 |
| WO | WO02/056931 | 7/2002 |

OTHER PUBLICATIONS

Dingley et al., "Blood volume determination by the carbon monoxide method using a new delivery system: accuracy in critically ill humans and precision in an animal model," *Crit Care Med.*, 27(11):2435-2441 (1999).

(Continued)

*Primary Examiner* — Robert L Nasser
(74) *Attorney, Agent, or Firm* — Lee & Hayes, PLLC

(57) ABSTRACT

The present invention relates to a method and apparatus for the administration of carbon monoxide (CO) to a patient. It allows the safe and effective use of carbon monoxide as a medicament.

16 Claims, 2 Drawing Sheets

U.S. PATENT DOCUMENTS

| | | | |
|---|---|---|---|
| 6,371,114 | B1 | 4/2002 | Schmidt et al. |
| 6,436,712 | B1 | 8/2002 | Yurgil et al. |
| 7,002,672 | B2 | 2/2006 | Tsuda |
| 2004/0084048 | A1 | 5/2004 | Stenzler et al. |
| 2004/0258772 | A1 | 12/2004 | Otterbein et al. |

OTHER PUBLICATIONS

Fujita et al., "Paradoxical rescue from ischemic lung injury by inhaled carbon monoxide driven by derepression of fibrinolysis," *Nature Medicine*, 7(5):598-604 (2001).

Motterlini et al., "Carbon monoxide-releasing molecules: characterization of biochemical and vascular activities," *Circ. Res.*, 90(2):E17-E24 (2002).

Wirth et al., Toxicology for Physicians, Scientists and Pharmacists, New York, Georg Thieme Verlag Stuttgart, (1985). (with translation).

Doeller, et al., Polarographic measurement of hydrogen sulfide production and consumption by mammalian tissues, Analytical Biochemistry 341 (2005) 40-51.

METHODS AND APPARATUS FOR THE ADMINISTRATION OF CO

CROSS-REFERENCE TO RELATED APPLICATIONS

This application is a continuation of patent application Ser. No. 10/520,270 filed Aug. 5, 2005 now U.S. Pat. No. 7,574,246, which is a National Stage of International Application No. PCT/EP2003/006856, filed Jun. 27, 2003, which claims the benefit of German Patent Application Serial No. 10230165.4, filed on Jul. 4, 2002. The disclosure of the prior applications are considered part of (and are incorporated by reference in) the disclosure of this application.

TECHNICAL FIELD

The present invention relates to a method and an apparatus for the administration of carbon monoxide to patients. More specifically, it relates to the controlled administration of carbon monoxide to a patient in order to achieve safe and effective use of carbon monoxide as a medicament.

BACKGROUND OF THE INVENTION

The therapeutic use of carbon monoxide (CO) has recently been the focus of scientific interest, and the medicinal effects of CO have been analyzed in animal experiments. Fujita et al. pointed to a link between CO and prevention of ischemic injury in mice, "Paradoxical rescue from ischemic lung injury by inhaled carbon monoxide driven by depression of fibrinolysis", *Nature medicine*, May 2001, 7, (5); p 598-604. Chapman et al. in "Carbon monoxide attenuates aeroallergen-induced inflammation in mice", *American Journal of Physiology*, July 2001, 281; (1); pL209-16 further pointed to an immunoregulatory role of CO in aeroallergen induced inflammation in mice.

WO 98/13058 (Pinsky et al.) claims methods of treating ischemic disorders comprising administering to the subject carbon monoxide gas in a sufficient amount over a sufficient period of time. Animal experiments using rats treated with CO prior to lung harvesting and transplantation of the harvested lung are reported. However, the application fails to provide any useful information as to how CO may be safely and effectively administered to individuals suffering from ischemia in a manner that ensures that the individual benefits from such treatment without being at risk of suffering from CO intoxication.

Gas-supply systems for the treatment of patients with controlled doses of medical gases are known in the art. For example, European patent 0 621 051 discloses an apparatus for the monitored metering of nitric oxide (NO) into the respiratory air of a patient.

WO 98/31282, the disclosure of which is incorporated herein by reference, discloses a controlled gas-supply system, in which one or several gases are added to the respiration gas of a patient at varying proportions by means of a control device, which device may offer a program control, a sensor control, or a combined sensor/program control. However, the application is silent regarding the possibility to administer a carbon monoxide containing gas. Consequently, it fails to provide any guidance as to how CO may be safely and effectively administered to individuals while avoiding the risk of CO intoxication.

A method or an apparatus for administration of therapeutic amounts of CO to an individual, human or animal, is not known from the prior art. Furthermore, a method and an apparatus whereby carbon monoxide can be safely and effectively administered to an individual is not known.

It is therefore an object of the present invention to provide a method and an apparatus for the safe and effective administration of carbon monoxide to patients. It is a further object to provide a method and an apparatus for such administration which avoid the risks which follow from the toxicity of carbon monoxide in humans and animals. Another object of the invention is to provide a method and apparatus for the administration of carbon monoxide to patients whereby the gas is administered in an effective way to achieve the best possible therapeutic effect of the gas.

These and further objects are solved by the methods and apparatuses as herein described and claimed.

SUMMARY OF THE INVENTION

Accordingly, in a first embodiment of the present invention, a method for administering carbon monoxide to a patient is provided, comprising the steps of
  a) administering exogenous carbon monoxide to the patient,
  b) determining the concentration of carbon monoxide in the patient's blood,
  c) comparing the actual concentration of carbon monoxide in the blood with a preset, desired value; and
  d) subsequently adjusting the amount of carbon monoxide delivered to the patient to obtain a concentration in the patient's blood corresponding to the preset desired value; and optionally
repeating steps b)-d).

In another aspect, the present invention provides an apparatus for administering carbon monoxide to a patient, the apparatus comprising a delivering unit for administering carbon monoxide to the patient, a carbon monoxide source, a dosing unit, sensor means for determining the concentration of carbon monoxide in the blood, and control means for regulating the dosing unit depending on feedback from the sensor unit.

In another aspect, the present invention provides in another aspect the use of a delivering unit, a carbon monoxide source, a dosing unit for administering carbon monoxide to a patient, a sensor means for determining the concentration of carbon monoxide in the blood, a control means for regulating a carbon monoxide dosing unit, or a filter unit suitable to remove excess carbon monoxide from expired gas, said filter being a physical or chemical filter, in any of the afore-mentioned methods according to the invention.

Finally, the present invention relates to the use of carbon monoxide or a carbon monoxide donor for the preparation of a medicament, for example an inhalable medicament, for the treatment of ischemia related conditions or the regulation of the immune response in a patient in need thereof by one of the methods according to the present invention.

DETAILED DESCRIPTION

Figure 1:
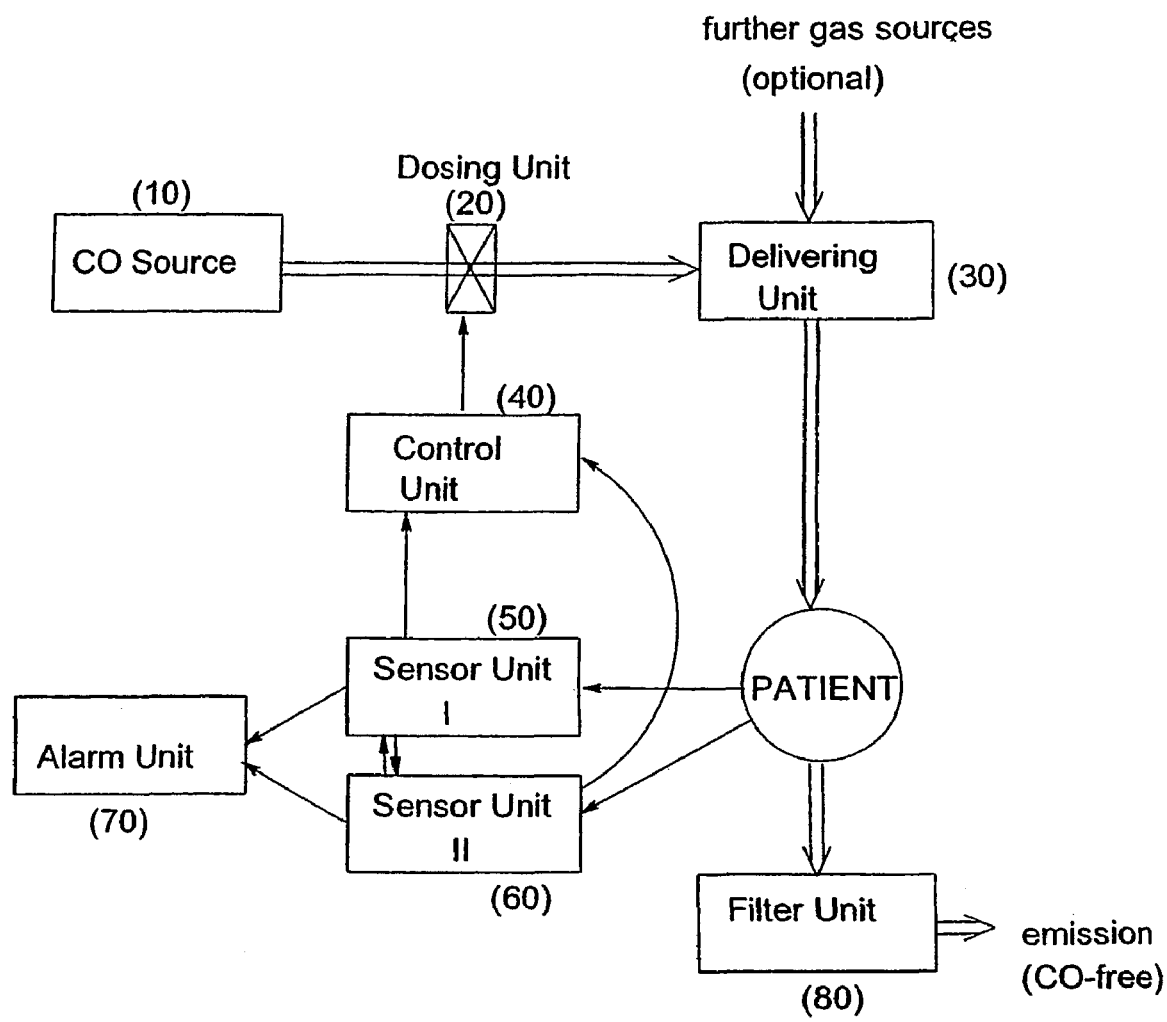
FIG. 1 shows a scheme of an apparatus according to a preferred embodiment of the present invention.

According to the invention, a carbon monoxide source comprises suitable storage units for carbon monoxide in gaseous form (optionally as a mixture comprising further gases, e.g., nitrogen, carbon dioxide, oxygen, argon, helium, sulfur hexafluoride, gaseous hydrocarbons, xenon), or in liquid form, or as a solution (e.g., in saline). Alternatively, the carbon monoxide may be provided in the form of a carbon monoxide donor. Said donor may comprise a gas, a liquid, a solid, or a solution.

A delivering unit according to the invention comprises medical devices suitable for the administration of gaseous or liquid medicaments to a patient. Those medical devices are known in the art and comprise, but are not limited to, e.g., a respirator, a ventilator, a nose cannula, a face mask (for the administration of gases), devices for the controlled administration of liquids by injection or infusion (for intravenous administration), devices for the controlled administration of liquids and/or gases by enema (for rectal administration), nebulizers (for the administration via nebulizing CO-releasing compounds and CO-releasing smoke) and conventional insufflation equipment (for the administration of gases via insufflation). It will further be understood that a delivering unit according to the invention may comprise means for the connection to a carbon monoxide source and/or a dosing unit, e.g., tubes, plug-ins, contacts, clamps and the like, the specific technical nature of these means depending on the delivering unit, the dosing unit and the carbon monoxide source actually employed.

A dosing unit according to the invention comprises technical means for the regulation of the quantity of carbon monoxide which is delivered from the carbon monoxide source to the delivering unit (and thus to the patient), wherein the quantity may be varied during the application. The technical nature of the dosing unit depends on the delivering unit and the carbon monoxide source actually employed. Suitable dosing units comprise, but are not limited to, e.g., one or several controllable valves or valve combinations or a relief valve.

Sensor means according to the invention comprises technical means for the determination of the concentration of carbon monoxide in the blood of a patient. Suitable sensor means comprise, but are not limited to, means for the measurement of carboxyhemoglobin or oxyhemoglobin or enzyme activity in the patient's blood by spectroscopic, polarographic or other methods, as well as means for the measurement of carbon monoxide in the gas mixture expired from a patient by spectroscopic methods or gas chromatography.

A control unit according to the invention comprises technical means for comparing the actual CO blood concentration directly or indirectly determined by the methods described herein with a preset desired value, and subsequently causing the dosing unit to regulate the amount of carbon monoxide delivered to the patient to obtain a concentration in the patient's blood corresponding to the preset desired value. The control unit may perform a program control, a sensor control, or a combined program/sensor control. Suitable control units comprise, but are not limited to, a conventional CPU (e.g., a discrete comparator, consisting of transistors or OP-amplifiers which compare the levels of a preset CO level and the CO level in the patient's blood).

Apparatuses and devices for the application of medicaments to a patient, which comprise at least two or more units as described above, are commercially available. It will be understood that such apparatuses and devices may also be employed for the purposes of the present invention. It will further be understood that the present invention also comprises the use of devices wherein at least two units as described above are combined into one single device. For example, a conventional respirator suitable for the present invention may serve as a dosing unit and as a delivering unit, although it is normally understood to be a single apparatus.

The present invention provides a method and apparatus for the safe administration of carbon monoxide to patients, wherein the concentration of carbon monoxide in the patient's blood is continuously monitored during the process, and the administration is continuously adjusted according to the current concentration.

For that purpose, after the first administration of carbon monoxide the concentration of carbon monoxide in the patient's blood is determined, and the actual concentration is compared to a preset, desired value. If the actual concentration is lower than the preset value, the carbon monoxide dose in the subsequent step(s) of administration is enhanced. If the actual concentration is higher than the preset value, the carbon monoxide dose in the subsequent step(s) of administration is reduced.

A preset value for the concentration of CO in the patient's blood according to this invention is between about 0.5% to 50%, preferably between 5% and 20%, more preferably between 5% and 15%, and most preferably about 8% (all values calculated as carboxyhemoglobin per total hemoglobin).

The preset value may also comprise a range of concentration, limited by a maximum value and a minimum value. If the concentration of carbon monoxide in the blood is outside this range, then the dosing will be adjusted.

Alternatively, in order to control and adjust the CO concentration in the patient's blood, it is also possible to reduce or enhance the concentration of oxygen in the patient's breathing gas, since the concentration of carbon monoxide and oxygen in the blood are connected via an equilibrium. Finally, the steps of administering, determining the CO blood concentration and adjusting the amount of carbon monoxide delivered to the patient may be repeated several times.

Several methods are known in the art that are suitable for the determination of carbon monoxide in the blood of a patient. One preferred method is to measure the concentration of carboxyhemoglobin (HbCO) in the blood. Such measurements can be performed in a non-invasive manner, e.g., by spectroscopic methods, e.g., as disclosed in U.S. Pat. Nos. 5,810,723 and 6,084,661 or in British patent No. GB 2,333,591, the disclosure of both documents being incorporated herein by reference. Invasive methods which include the step of taking a blood sample are, of course, likewise suitable.

Since an equilibrium exists between the concentrations of oxygen and carbon monoxide in the blood, another preferred method is to measure the concentration of oxygen in the blood (oxymetry) and to calculate the carbon monoxide concentration from the equilibrium constant. The oxymetric measurement can be performed in a non-invasive manner by spectroscopic determination of oxyhemoglobin concentration in the blood, e.g., as disclosed in European patent No. 0 524 083 or U.S. Pat. No. 5,413,100, the disclosure of both documents being incorporated herein by reference. Another possibility for oxymetric measurements is the employment of polarographic methods which are well-established in the art. Again, invasive methods which include the step of taking a blood sample are, of course, likewise suitable to determine the concentration of oxygen in the blood.

Although the best-known reaction of carbon monoxide incorporated in a human or animal body is the formation of carboxyhemoglobin, it can also interact with other biological targets such as enzymes, e.g. cytochrome oxidase or NADPh. Activity measurements regarding these enzymes may thus also be employed for calculating the carbon monoxide concentration in the blood.

There is an equilibrium regarding the distribution of carbon monoxide between blood and the respired gas mixture. Another preferred method for determining the blood concentration of CO is thus the measurement of the carbon monoxide concentration in the expired air of a patient. This measurements may be done by spectroscopic methods, e.g., by ultra red absorption spectroscopy (URAS), or by gas chromatography. This method of determination is well-established in medical art for the determination of the diffusing capacity of the lungs of a patient; an apparatus for those tests is disclosed in U.S. Pat. No. 5,022,406, the disclosure of which is incorporated herein by reference. Alternatively, the measurements of CO concentration may be carried out by electrochemical methods known in the art.

As mentioned above, the high toxicity of carbon monoxide makes it necessary to ensure that the dosage of CO is always kept at levels that ensure sufficient metabolic activity in the individual treated. The present invention provides for the first time methods and apparatuses that avoid the risk of CO intoxication. Preferably, the concentration of CO in the blood is determined by at least two independent methods of measurement. More preferably, the first method of measurement is the spectroscopic measurement of carboxyhemoglobin in the patient's blood, which may be combined with the spectroscopic measurement of oxyhemoglobin or the measurement of the CO concentration in the expired air from the patient.

Additionally, it is preferred that the measuring unit(s) is connected to an alarm unit, which is activated if, e.g., the carbon monoxide concentration in the patient's blood exceeds a preset desired value. Additionally, in the case described above wherein at least two independent methods of measurement are employed, the alarm unit may be activated if the carbon monoxide concentration derived by the first method shows a difference to that derived by the second method that exceeds a preset desired value.

When using carbon monoxide as a medicament as described above, it has to be considered that the carbon monoxide is eliminated from the patient mainly by expiration via the lungs, resulting in an enhanced concentration of carbon monoxide in the surrounding air, if the carbon monoxide is not removed from the expired air. Accordingly, in a preferred embodiment, the method and apparatus of the present invention employ a filter device to remove CO from the air expired by the patient. The filter device may remove the carbon monoxide by physical effects, e.g., by dissolving the CO in a suitable solvent or adsorbing CO on a suitable adsorber material, or by chemical effects, e.g., by oxidation of CO to $CO_2$ by using a suitable catalyst. Filter devices as described above are known in the art, e.g., molecular separators, gas purifiers or wet gas cleaners may be employed.

An example of an apparatus according to the present invention is shown in FIG. 1, wherein the apparatus comprises a CO source (10), which is connected to a delivering unit (30). The mass flow between the CO source (10) and the delivering unit (30) is controlled by a dosing unit (20). The CO is administered to the patient by the delivering unit (30), while the air expired by the patient is cleaned by passing it through the filter unit (80). The concentration of carbon monoxide in the patient's blood is independently measured by two sensor units (50, 60), which are both independently connected to the alarm unit (70). Both sensor units are furthermore independently connected to the control unit (40), which regulates the dosing unit (20) in order to ensure a controlled delivery of CO to the patient, which depends on the actual concentration of CO in the patient's blood.

Carbon monoxide at normal conditions is a gaseous compound. The admixing of carbon monoxide into the breathing air (or a breathing gas mixture different from air) for inhalation of a patient may thus be considered to be a convenient manner of application according to the invention. However, carbon monoxide may also suitably be administered for the purposes of this invention by insufflation or as a solution in pharmaceutically acceptable liquids via intravenous or rectal application. Alternatively, it can be administered in the form of carbon monoxide donor compounds, which release the CO after the application. A donor compound suitable for this invention may comprise either a carrier, e.g., extracorporeal (synthetic) carboxyhemoglobin, or a compound that is metabolised to CO, e.g. methylene chloride ($CH_2Cl_2$) or heme oxygenase.

For the administration of the carbon monoxide containing gas mixture a conventional respirator apparatus, a ventilator, a face mask or a nose cannula may be employed.

Figure 2:
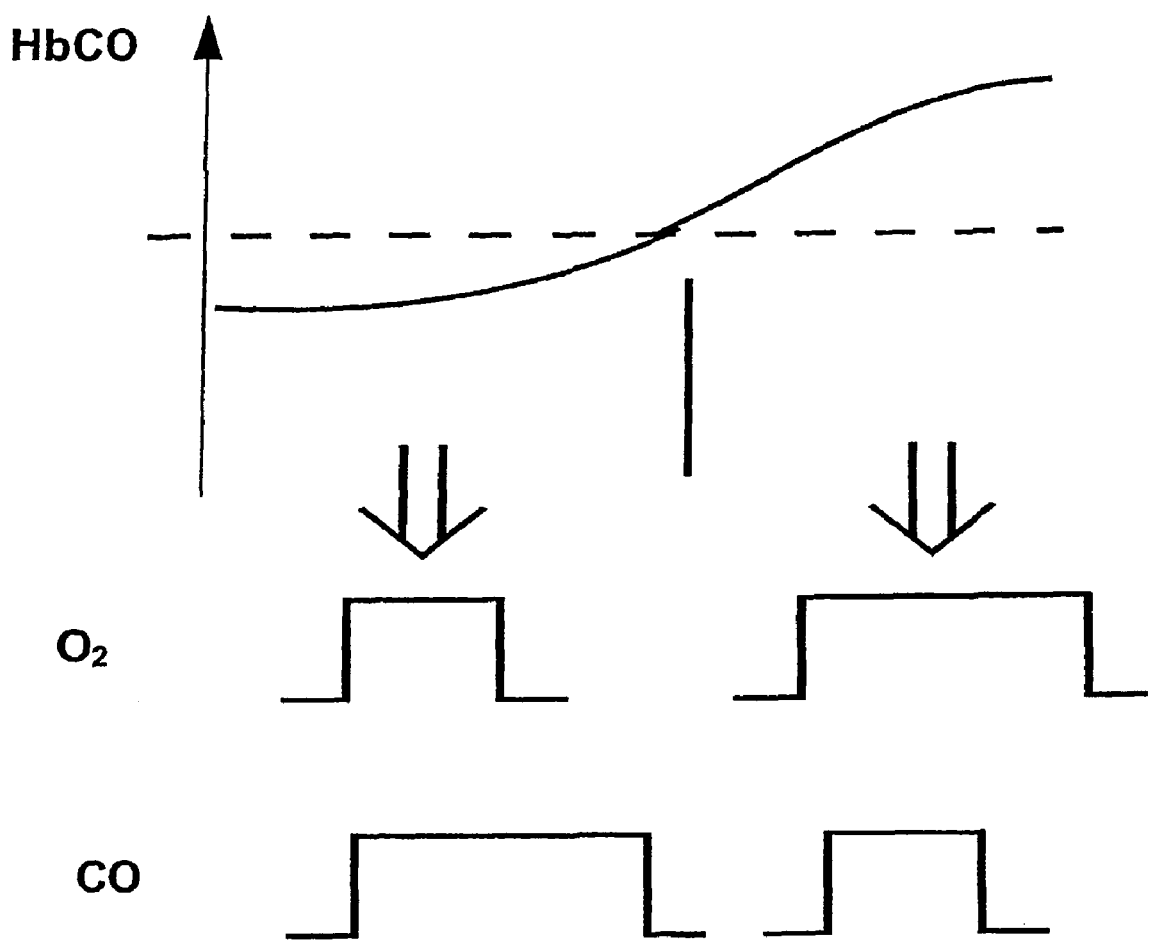
FIG. 2 shows dosing curves for CO and $O_2$ in correlation with the concentration of carboxyhemoglobin in the patient's blood (straight line) and a preset value for the carboxyhemoglobin concentration (dotted line) in an embodiment according to the present invention.

The carbon monoxide may be administered to the patient in a continuous or discontinuous manner. In particular, a pulsed administration is suitable according to the present invention, in particular wherein the pulses are combined to pulse sequences. If the carbon monoxide is administered by admixing gaseous carbon monoxide into the breathing gas mixture of a patient, the pulses may be triggered by inspiration or expiration. Additionally, the number and length of the single pulses may be determined by the current concentration of CO in the patient's blood. An example for a variation of the pulse length depending on the CO concentration is given in FIG. 2. Alternatively, the regulation of the amount of CO in the breathing gas mixture may be performed by varying the CO flow when the CO is administered in a continuous manner. The patient may breath spontaneously or artificially.

Additionally, dosing algorithms may be employed in order to obtain different dosages at different times of the therapy. For example, a high concentration of CO may be administered at the beginning of the treatment, a (lower) constant concentration may be administered during therapy, while at the end the concentration is again lowered. The administered dosages are thus dependent on the duration of the therapy and the actual concentration of CO in the blood.

The invention claimed is:

1. A method for administering carbon monoxide to a patient, comprising the steps of:
   a) administering exogenous carbon monoxide to the patient,
   b) determining the concentration of carbon monoxide in the patient's blood,
   c) comparing the actual concentration of carbon monoxide in the blood with a preset, desired value using a central processing unit;
   and optionally repeating steps b)-d)
   wherein the administration of carbon monoxide is performed via sequences of pulses, wherein the number and length of the pulses in each sequence and/or the number of sequences is regulated depending on the determination of the concentration of carbon monoxide in the blood,
   wherein the carbon monoxide is delivered to a patient as a pure gas, in a gas mixture, dissolved in a fluid, or by administering a carbon monoxide donor, and,
   wherein the carbon monoxide containing gas mixture is administered by way of admixing it into the breathing air of a patient.

2. The method according to claim 1 wherein the concentration of carbon monoxide in the blood is determined by a method selected from the group consisting of:

measuring the concentration of carboxyhemoglobin (HbCO) in the blood, measuring the concentration of oxyhemoglobin (HbO2) in the blood, measuring the activity of enzymes in the blood; and measuring the CO content of the air expired by the patient.

3. The method according to claim 2 wherein the carboxyhemoglobin (HbCO) is determined by non-invasive measurement, or is determined from a blood sample.

4. The method according to claim 2 wherein the measurement of the oxyhemoglobin (HbO2) in the blood is carried out by oxymetry.

5. The method according to claim 2 wherein a measurement of the composition of the expired air is carried out by spectroscopic or electrochemical methods.

6. The method according to claim 1 wherein the carbon monoxide is delivered to the patient through inhalation, insufflation, intravenously, or rectally.

7. The method according to claim 6 wherein the carbon monoxide is delivered for inhalation in pulses, wherein the pulses may be inspiration and/or expiration triggered.

8. The method according to claim 1 wherein the concentration of carbon monoxide in the blood is controlled by the oxygen content of the breathing gas.

9. The method according to claim 1 wherein the patient is spontaneously breathing or artificially breathing.

10. The method according to claim 1 wherein the concentration of carbon monoxide in the blood is determined by at least two separate methods of measurement.

11. An apparatus for administering carbon monoxide to a patient, the apparatus comprising:

a delivering unit, a carbon monoxide source, a dosing unit for administering carbon monoxide to the patient, sensor means for regulating the dosing unit depending on the feedback from the sensor unit, and, a filter unit through which the air expired by the patient is passed in order to remove excess carbon monoxide from the expired gas, wherein the filter is a physical or a chemical filter.

12. The apparatus according to claim 11 wherein the carbon monoxide source is providing carbon monoxide gas, optionally in a mixture with one or more other gases, and wherein the dosing unit is for administering the carbon monoxide gas or the carbon monoxide containing gas mixture into the breathing gas mixture of a patient.

13. The apparatus according to claim 11 wherein the delivering unit is selected from the group consisting of a respirator, a ventilator, a face mask, and a nose cannula.

14. The apparatus according to claim 11 wherein the apparatus comprises at least two independently working sensor means for determination of carbon monoxide in the blood.

15. The apparatus according to claim 11 wherein at least one of the sensor means is connected to an alarm unit.

16. The apparatus according to claim 11 wherein the sensor means are selected from the group consisting of:

means for measuring the concentration of carboxyhemoglobin (HbCO), means for measuring the concentration of oxyhemoglobin (HbO2) in the blood, means for measuring the activity of enzymes in the blood, and means for measuring the composition of the air expired by the patient.

* * * * *